United States Patent
Wang et al.

(10) Patent No.: US 10,655,117 B2
(45) Date of Patent: May 19, 2020

(54) PULLULANASE AND USE THEREOF

(71) Applicant: Beijing Jinhong Tianbang Information Technology Co., ltd, Beijing (CN)

(72) Inventors: Yu Wang, Tianjin (CN); Litong Ban, Tianjin (CN); Liang Huang, Tianjin (CN); Ning Sun, Tianjin (CN); Hongpeng Yang, Tianjin (CN)

(73) Assignee: BEIJING HONGMING XINDA TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/029,647

(22) Filed: Jul. 9, 2018

(65) Prior Publication Data
US 2019/0010474 A1    Jan. 10, 2019

(30) Foreign Application Priority Data

May 29, 2018   (CN) .......................... 2018 1 0527491

(51) Int. Cl.
| | | |
|---|---|---|
| *C12N 9/44* | (2006.01) | |
| *C12N 9/24* | (2006.01) | |
| *C12N 15/74* | (2006.01) | |
| *C12N 15/52* | (2006.01) | |
| *C12R 1/84* | (2006.01) | |
| *C12P 19/02* | (2006.01) | |
| *C12P 19/14* | (2006.01) | |
| *C07H 21/04* | (2006.01) | |

(52) U.S. Cl.
CPC ........... *C12N 9/2457* (2013.01); *C12N 15/52* (2013.01); *C12N 15/74* (2013.01); *C12P 19/02* (2013.01); *C12P 19/14* (2013.01); *C12R 1/84* (2013.01); *C12Y 302/01041* (2013.01)

(58) Field of Classification Search
CPC .................... C12N 15/52; C12N 15/74; C12Y 302/01041; C12P 19/14; C12P 19/02
USPC ... 435/69.1, 320.1, 161, 252.3, 254.23, 200; 536/23.2
See application file for complete search history.

(56) References Cited

PUBLICATIONS

Turkenburg et al. Proteins, 2009, pp. 516-519.*

* cited by examiner

*Primary Examiner* — Robert B Mondesi
*Assistant Examiner* — Mohammad Y Meah
(74) *Attorney, Agent, or Firm* — Tony C. Hom, Esq.

(57) ABSTRACT

The present application relates to the field of enzyme engineering, especially relates to a pullulanase as well as preparation and use thereof. The pullulanase and coding gene thereof were obtained by random mutation by using the Error-prone PCR technique on the gene of wild-type pullulanase to obtain a mutant PLUM. The enzyme activity of the mutant PLUM was improved by 57.03% compared with the wild-type pullulanase PLUM.

1 Claim, 1 Drawing Sheet

Specification includes a Sequence Listing.

SEQUENCE LISTING

<160> NUMBER OF SEQ ID NOS: 8

<210> SEQ ID NO 1
<211> LENGTH: 2766
<212> TYPE: DNA
<213> ORGANISM: Artificial Sequence
<220> FEATURE:
<223> OTHER INFORMATION: synthetic

<400> SEQUENCE: 1

| | | | | | | |
|---|---|---|---|---|---|---|
| gacagcacca | gtaccaaggt | catcgtccac | taccacagat | tcgacagtaa | ttacaccaac | 60 |
| tgggatgttt | ggatgtggcc | ataccaacca | gtcaacggaa | acggtgctgc | atatcagttt | 120 |
| actggaacca | acgacgactt | cggtgcagtc | gctgacactc | aggttccagg | tgacaacacc | 180 |
| caggtcggtc | tcatcgtcag | aaagaacgac | tggtctgaga | gaacactcc | taatgacttg | 240 |
| cacatcgact | tggctaaggg | tcacgaggtc | tggatcgtcc | agggtgatcc | taccatctac | 300 |
| tataaccttt | ctgatgctca | agcagctgcc | atccctagcg | tcagcaacgc | ttacttggac | 360 |
| gacgagaaga | ctgtcttggc | taaactgtcc | atgccaatga | ctcttgctga | cgcagcctct | 420 |
| ggtttcactg | tcatcgacaa | gactactgga | gagaagattc | cagttactag | cgcagtcagt | 480 |
| gccaacccag | tcactgctgt | cttggtcggt | gatcttcagc | aagcacttgg | tgctgctaac | 540 |
| aactggagtc | ctgacgacga | ccataccttg | ttgaagaaaa | tcaaccctaa | cttgtatcag | 600 |
| cttagtggca | ccttgcctgc | tggcacttat | cagtacaaaa | tcgctcttga | tcacagctgg | 660 |
| aacaccagtt | accctggcaa | taacgtctcc | ttgaccgtcc | cagagggtgg | tgagaaagtc | 720 |
| actttcactt | acatccctag | cactaaccaa | gtctttgact | ctgttaacca | cccaaatcag | 780 |
| gcttttccaa | ccagtagtgc | tggtgttcaa | accaaccttg | ttcagcttac | ccttgcttct | 840 |
| gctcctgacg | ttactcacaa | cctggacgtc | gctgctgatg | gctataaggc | tcataacatc | 900 |
| cttccaagaa | acgtcctgaa | ccttccaaga | tacgactact | ctggcaacga | ccttggcaac | 960 |
| gtctacagca | agacgctac | cagtttcaga | gtctgggcac | ctactgccag | taacgttcaa | 1020 |
| ctcttgctct | ataactccga | gaagggaagt | atcaccaagc | aacttgagat | gcagaagtcc | 1080 |
| gacaatggaa | cctggaagct | ccaagtcagt | ggcaacttgg | agaattggta | ctacttgtac | 1140 |
| caggttactg | tcaatggtac | tacccagact | gctgttgacc | cttacgctag | agccatcagt | 1200 |
| gtcaacgcta | ccagaggcat | gatcgttgat | ctcaaggcta | ctgatccagc | tggttggcaa | 1260 |
| ggagaccacg | agcaaactcc | agctaaccct | gttgacgagg | tcatctacga | agctcacgtc | 1320 |
| agagacttca | gtatcgacgc | aaacagtggc | atgaagaaca | aaggtaagta | ccttgccttc | 1380 |
| actgaacatg | gcaccaaagg | tcctgatcac | gtcaaaactg | gcatcgactc | tctcaaagag | 1440 |
| cttggtatta | ctaccgtcca | gcttcagcca | gtcgaagagt | tcaactccat | cgacgaaact | 1500 |
| caaccagaca | cttacaattg | gggttatgac | cctagaaact | acaatgttcc | tgaaggtgcc | 1560 |
| tacgctacca | ctcctgaggg | tactgctaga | atcaccgaac | tcaaacagct | catccagtcc | 1620 |
| ttgcaccaac | aaagaatcgg | tgtcaacatg | gacgtcgtct | acaaccacac | tttcgacgtc | 1680 |
| atggtcagcg | acttcgacaa | gatcgttcca | cagtactact | acagaactga | ctccaacggt | 1740 |
| aactacacta | atggctctgg | ctgtggtaac | gagtttgcta | ctgaacatcc | tatggctcag | 1800 |
| aagttcgtct | tggactccgt | caactactgg | gtcaacgaat | atcatgttga | cggtttcaga | 1860 |
| ttcgatctta | tggccttgct | tggcaaggat | actatggcta | agatcagcaa | cgaacttcac | 1920 |
| gctatcaatc | caggcatcgt | cctttacggt | gagccttgga | ctggtggcac | cagtggtctt | 1980 |
| agctctgatc | agttggtcac | taaaggccag | cagaaaggtc | ttggcatcgg | tgtctttaac | 2040 |

```
gacaacatca gaaacggttt ggacggtaat gtcttcgaca agactgctca gggtttcgct    2100
actggtgatc ctaaccaagt tgacgtcatc aagaacggtg tcattggctc catccaggac    2160
ttcaccagtg ctccatctga gaccatcaat tacgtcactt ctcacgacaa tatgactttg    2220
tgggacaaga tccttgcttc caacccttcc gataccgaag cagatagaat caagatggac    2280
gagcttgctc acgctgtcgt ctttaccagt cagggtgttc ctttcatgca gggaggtgag    2340
gagatgctta gaaccaaagg tggtaacgac aattcctaca atgctggtga ctccgtcaac    2400
cagtttgatt ggagtagaaa ggctcagttc aaggacgtct tcgactattt cagctccatg    2460
atccacttga gaaaccaaca tccagctttc agaatgacca ctgctgacca gatcaagcag    2520
aacttgacct tcttgagtc tcctaccaat actgtcgcat ttgaactcaa gaactacgct    2580
aatcacgaca cctggaagaa catcatcgtt atgtacaatc ctaacaaaac cagtcagact    2640
ttgaacttgc cttctggtga ctggactatc gtcggtcttg gtgatcagat cggagaaaag    2700
agccttggac acgtcatggg taacgtccag gtcccagcca tctccacttt gatccttaag    2760
cagtaa                                                               2766

<210> SEQ ID NO 2
<211> LENGTH: 921
<212> TYPE: PRT
<213> ORGANISM: Artificial Sequence
<220> FEATURE:
<223> OTHER INFORMATION: synthetic

<400> SEQUENCE: 2

Asp Ser Thr Ser Thr Lys Val Ile Val His Tyr His Arg Phe Asp Ser
1               5                   10                  15

Asn Tyr Thr Asn Trp Asp Val Trp Met Trp Pro Tyr Gln Pro Val Asn
            20                  25                  30

Gly Asn Gly Ala Ala Tyr Gln Phe Thr Gly Thr Asn Asp Asp Phe Gly
        35                  40                  45

Ala Val Ala Asp Thr Gln Val Pro Gly Asp Asn Thr Gln Val Gly Leu
    50                  55                  60

Ile Val Arg Lys Asn Asp Trp Ser Glu Lys Asn Thr Pro Asn Asp Leu
65                  70                  75                  80

His Ile Asp Leu Ala Lys Gly His Glu Val Trp Ile Val Gln Gly Asp
                85                  90                  95

Pro Thr Ile Tyr Tyr Asn Leu Ser Asp Ala Gln Ala Ala Ile Pro
            100                 105                 110

Ser Val Ser Asn Ala Tyr Leu Asp Asp Glu Lys Thr Val Leu Ala Lys
        115                 120                 125

Leu Ser Met Pro Met Thr Leu Ala Asp Ala Ser Gly Phe Thr Val
    130                 135                 140

Ile Asp Lys Thr Thr Gly Glu Lys Ile Pro Val Thr Ser Ala Val Ser
145                 150                 155                 160

Ala Asn Pro Val Thr Ala Val Leu Val Gly Asp Leu Gln Gln Ala Leu
                165                 170                 175

Gly Ala Ala Asn Asn Trp Ser Pro Asp Asp His Thr Leu Leu Lys
            180                 185                 190

Lys Ile Asn Pro Asn Leu Tyr Gln Leu Ser Gly Thr Leu Pro Ala Gly
        195                 200                 205

Thr Tyr Gln Tyr Lys Ile Ala Leu Asp His Ser Trp Asn Thr Ser Tyr
    210                 215                 220
```

-continued

Pro Gly Asn Asn Val Ser Leu Thr Val Pro Glu Gly Glu Lys Val
225                 230                 235                 240

Thr Phe Thr Tyr Ile Pro Ser Thr Asn Gln Val Phe Asp Ser Val Asn
            245                 250                 255

His Pro Asn Gln Ala Phe Pro Thr Ser Ser Ala Gly Val Gln Thr Asn
        260                 265                 270

Leu Val Gln Leu Thr Leu Ala Ser Ala Pro Asp Val Thr His Asn Leu
    275                 280                 285

Asp Val Ala Ala Asp Gly Tyr Lys Ala His Asn Ile Leu Pro Arg Asn
290                 295                 300

Val Leu Asn Leu Pro Arg Tyr Asp Tyr Ser Gly Asn Asp Leu Gly Asn
305                 310                 315                 320

Val Tyr Ser Lys Asp Ala Thr Ser Phe Arg Val Trp Ala Pro Thr Ala
            325                 330                 335

Ser Asn Val Gln Leu Leu Tyr Asn Ser Glu Lys Gly Ser Ile Thr
        340                 345                 350

Lys Gln Leu Glu Met Gln Lys Ser Asp Asn Gly Thr Trp Lys Leu Gln
    355                 360                 365

Val Ser Gly Asn Leu Glu Asn Trp Tyr Tyr Leu Tyr Gln Val Thr Val
370                 375                 380

Asn Gly Thr Thr Gln Thr Ala Val Asp Pro Tyr Ala Arg Ala Ile Ser
385                 390                 395                 400

Val Asn Ala Thr Arg Gly Met Ile Val Asp Leu Lys Ala Thr Asp Pro
            405                 410                 415

Ala Gly Trp Gln Gly Asp His Glu Gln Thr Pro Ala Asn Pro Val Asp
        420                 425                 430

Glu Val Ile Tyr Glu Ala His Val Arg Asp Phe Ser Ile Asp Ala Asn
    435                 440                 445

Ser Gly Met Lys Asn Lys Gly Lys Tyr Leu Ala Phe Thr Glu His Gly
450                 455                 460

Thr Lys Gly Pro Asp His Val Lys Thr Gly Ile Asp Ser Leu Lys Glu
465                 470                 475                 480

Leu Gly Ile Thr Thr Val Gln Leu Gln Pro Val Glu Glu Phe Asn Ser
            485                 490                 495

Ile Asp Glu Thr Gln Pro Asp Thr Tyr Asn Trp Gly Tyr Asp Pro Arg
        500                 505                 510

Asn Tyr Asn Val Pro Glu Gly Ala Tyr Ala Thr Thr Pro Glu Gly Thr
    515                 520                 525

Ala Arg Ile Thr Glu Leu Lys Gln Leu Ile Gln Ser Leu His Gln Gln
530                 535                 540

Arg Ile Gly Val Asn Met Asp Val Val Tyr Asn His Thr Phe Asp Val
545                 550                 555                 560

Met Val Ser Asp Phe Asp Lys Ile Val Pro Gln Tyr Tyr Arg Thr
            565                 570                 575

Asp Ser Asn Gly Asn Tyr Thr Asn Gly Ser Gly Cys Gly Asn Glu Phe
        580                 585                 590

Ala Thr Glu His Pro Met Ala Gln Lys Phe Val Leu Asp Ser Val Asn
    595                 600                 605

Tyr Trp Val Asn Glu Tyr His Val Asp Gly Phe Arg Phe Asp Leu Met
610                 615                 620

Ala Leu Leu Gly Lys Asp Thr Met Ala Lys Ile Ser Asn Glu Leu His
625                 630                 635                 640

Ala Ile Asn Pro Gly Ile Val Leu Tyr Gly Glu Pro Trp Thr Gly Gly

```
                  645                 650                 655
Thr Ser Gly Leu Ser Ser Asp Gln Leu Val Thr Lys Gly Gln Gln Lys
            660                 665                 670
Gly Leu Gly Ile Gly Val Phe Asn Asp Asn Ile Arg Asn Gly Leu Asp
            675                 680                 685
Gly Asn Val Phe Asp Lys Thr Ala Gln Gly Phe Ala Thr Gly Asp Pro
            690                 695                 700
Asn Gln Val Asp Val Ile Lys Asn Gly Val Ile Gly Ser Ile Gln Asp
705                 710                 715                 720
Phe Thr Ser Ala Pro Ser Glu Thr Ile Asn Tyr Val Thr Ser His Asp
                725                 730                 735
Asn Met Thr Leu Trp Asp Lys Ile Leu Ala Ser Asn Pro Ser Asp Thr
            740                 745                 750
Glu Ala Asp Arg Ile Lys Met Asp Glu Leu Ala His Ala Val Val Phe
            755                 760                 765
Thr Ser Gln Gly Val Pro Phe Met Gln Gly Gly Glu Glu Met Leu Arg
            770                 775                 780
Thr Lys Gly Gly Asn Asp Asn Ser Tyr Asn Ala Gly Asp Ser Val Asn
785                 790                 795                 800
Gln Phe Asp Trp Ser Arg Lys Ala Gln Phe Lys Asp Val Phe Asp Tyr
                805                 810                 815
Phe Ser Ser Met Ile His Leu Arg Asn Gln His Pro Ala Phe Arg Met
            820                 825                 830
Thr Thr Ala Asp Gln Ile Lys Gln Asn Leu Thr Phe Leu Glu Ser Pro
            835                 840                 845
Thr Asn Thr Val Ala Phe Glu Leu Lys Asn Tyr Ala Asn His Asp Thr
            850                 855                 860
Trp Lys Asn Ile Ile Val Met Tyr Asn Pro Asn Lys Thr Ser Gln Thr
865                 870                 875                 880
Leu Asn Leu Pro Ser Gly Asp Trp Thr Ile Val Gly Leu Gly Asp Gln
                885                 890                 895
Ile Gly Glu Lys Ser Leu Gly His Val Met Gly Asn Val Gln Val Pro
            900                 905                 910
Ala Ile Ser Thr Leu Ile Leu Lys Gln
            915                 920

<210> SEQ ID NO 3
<211> LENGTH: 2766
<212> TYPE: DNA
<213> ORGANISM: Artificial Sequence
<220> FEATURE:
<223> OTHER INFORMATION: synthetic

<400> SEQUENCE: 3
gacagcacca gtaccaaggt catcgtccac taccacagat tcgacagtaa ttacaccaac      60
tgggatgttt ggatgtggcc ataccaacca gtcaacggaa acgtgctgc atatcagttt      120 actggaacca acgacgactt cggtgcagtc gctgacactc aggttccagg tgacaacacc      180
caggtcggtc tcatcgtcag aaagaacgac tggtctgaga agaacactcc taatgacttg      240
cacatcgact ggctaagggg tcacgaggtc tggatcgtcc agggtgatcc taccatctac      300
tataaccttt ctgatgctca agcagctgcc atccctagcg tcagcaacgc ttacttggac      360
gacgagaaga ctgtcttggc taaactgtcc atgccaatga ctcttgctga cgcagcctct      420
ggtttcactg tcatcgacaa gactactgga gagaagattc cagttactag cgcagtcagt      480
```

```
gccaacccag tcactgctgt cttggtcggt gatcttcagc aagcacttgg tgctgctaac    540
aactggagtc ctgacgacga ccataccttg ttgaagaaaa tcaaccctaa cttgtatcag    600
cttagtggca ccttgcctgc tggcacttat cagtacaaaa tcgctcttga tcacagctgg    660
aacaccagtt accctggcaa taacgtctcc ttgaccgtcc cagagggtgg tgagaaagtc    720
actttcactt acatccctag cactaaccaa gtctttgact ctgttaacca cccaaatcag    780
gcttttccaa ccagtagtgc tggtgttcaa accaaccttg ttcagcttac ccttgcttct    840
gctcctgacg ttactcacaa cctggacgtc gctgctgatg gctataaggc tcataacatc    900
cttccaagaa acgtcctgaa ccttccaaga tacgactact ctggcaacga ccttggcaac    960
gtctacagca aagacgctac cagtttcaga gtctgggcac ctactgccag taacgttcaa   1020
ctcttgctct ataactccga aagggaagt atcaccaagc aacttgagat gcagaagtcc   1080
gacaatggaa cctggaagct ccaagtcagt ggcaacttgg agaattggta ctacttgtac   1140
caggttactg tcaatggtac tacccagact gctgttgacc cttacgctag agccatcagt   1200
gtcaacgcta ccagaggcat gatcgttgat ctcaaggcta ctgatccagc tggttggcaa   1260
ggagaccacg agcaaaactc cagctaaccct gttgacgagg tcatctacga agctcacgtc   1320
agagacttca gtatcgacgc aaacagtggc atgaagaaca aggtaagta ccttgccttc   1380
actgaacatg gcaccaaagg tcctgatcac gtcaaaactg gcatcgactc tctcaaagag   1440
cttggtatta ctaccgtcca gcttcagcca gtcgaagagt tcaactccat cgacgaaact   1500
caaccagaca cttacaattg gggttatgac cctagaaact acaatgttcc tgaaggtgcc   1560
tacgctacca ctcctgaggg tactgctaga atcaccgaac tcaaacagct catccagtcc   1620
ttgcaccaac aaagaatctg tgtcaccatg gacgtcgtct acaaccacac tttcgacgtc   1680
atggtcagcg acttcgacaa gatcgttcca cagtactact acagaactga ctccaacggt   1740
aactacacta atggctctgg ctgtggtaac gagtttgcta ctgaacatcc tatggctcag   1800
aagttcgtct ggactccgt caactactgg gtcaacgaat atcatgttga cggtttcaga   1860
ttcgatttta tggccttgct tggcaaggat actatggcta agatcagcaa cgaacttcac   1920
gctatcaatc caggcatcgt cctttacggt gagccttgga ctggtggcac cagtggtctt   1980
agctctgatc agttggtcac taaaggccag cagaaaggtc ttggcatcgg tgtctttaac   2040
gacaacatca gaaacggttt ggacggtaat gtcttcgaca agactgctca gggtttcgct   2100
actggtgatc ctaaccaagt tgacgtcatc aagaacggtg tcattggctc catccaggac   2160
ttcaccagtg ctccatctga gaccatcaat acgtcacttt tcacgacaa tatgactttg   2220
tgggacaaga tccttgcttc caacccttcc gataccgaag cagatagaat caagatggac   2280
gagcttgctc acgctgtcgt ctttaccagt cagggtgttc cttcatgca gggaggtgag   2340
gagatgctta gaaccaaagg tggtaacgac aattcctaca atgctggtga ctccgtcaac   2400
cagtttgatt ggagtagaaa ggctcagttc aaggacgtct tcgactattt cagctccatg   2460
atccacttga gaaccaaca tccagctttc agaatgacca ctgctgacca gatcaagcag   2520
aacttgacct tcttgagtc tcctaccaat actgtcgcat tgaactcaa gaactacgct   2580
aatcacgaca cctggaagaa catcatcgtt atgtacaatc taacaaaac cagtcagact   2640
ttgaacttgc cttctggtga ctggactatc gtcggtcttg gtgatcagat cggagaaaag   2700
agccttggac acgtcatggg taacgtccag gtcccagcca tctccacttt gatccttaag   2760
cagtaa                                                              2766
```

<210> SEQ ID NO 4
<211> LENGTH: 921
<212> TYPE: PRT
<213> ORGANISM: Artificial Sequence
<220> FEATURE:
<223> OTHER INFORMATION: synthetic

<400> SEQUENCE: 4

```
Asp Ser Thr Ser Thr Lys Val Ile Val His Tyr His Arg Phe Asp Ser
1               5                   10                  15

Asn Tyr Thr Asn Trp Asp Val Trp Met Trp Pro Tyr Gln Pro Val Asn
            20                  25                  30

Gly Asn Gly Ala Ala Tyr Gln Phe Thr Gly Thr Asn Asp Asp Phe Gly
        35                  40                  45

Ala Val Ala Asp Thr Gln Val Pro Gly Asp Asn Thr Gln Val Gly Leu
    50                  55                  60

Ile Val Arg Lys Asn Asp Trp Ser Glu Lys Asn Thr Pro Asn Asp Leu
65                  70                  75                  80

His Ile Asp Leu Ala Lys Gly His Glu Val Trp Ile Val Gln Gly Asp
                85                  90                  95

Pro Thr Ile Tyr Tyr Asn Leu Ser Asp Ala Gln Ala Ala Ile Pro
            100                 105                 110

Ser Val Ser Asn Ala Tyr Leu Asp Asp Glu Lys Thr Val Leu Ala Lys
        115                 120                 125

Leu Ser Met Pro Met Thr Leu Ala Asp Ala Ala Ser Gly Phe Thr Val
    130                 135                 140

Ile Asp Lys Thr Thr Gly Glu Lys Ile Pro Val Thr Ser Ala Val Ser
145                 150                 155                 160

Ala Asn Pro Val Thr Ala Val Leu Val Gly Asp Leu Gln Gln Ala Leu
                165                 170                 175

Gly Ala Ala Asn Asn Trp Ser Pro Asp Asp His Thr Leu Leu Lys
            180                 185                 190

Lys Ile Asn Pro Asn Leu Tyr Gln Leu Ser Gly Thr Leu Pro Ala Gly
        195                 200                 205

Thr Tyr Gln Tyr Lys Ile Ala Leu Asp His Ser Trp Asn Thr Ser Tyr
    210                 215                 220

Pro Gly Asn Asn Val Ser Leu Thr Val Pro Glu Gly Gly Glu Lys Val
225                 230                 235                 240

Thr Phe Thr Tyr Ile Pro Ser Thr Asn Gln Val Phe Asp Ser Val Asn
                245                 250                 255

His Pro Asn Gln Ala Phe Pro Thr Ser Ser Ala Gly Val Gln Thr Asn
            260                 265                 270

Leu Val Gln Leu Thr Leu Ala Ser Ala Pro Asp Val Thr His Asn Leu
        275                 280                 285

Asp Val Ala Ala Asp Gly Tyr Lys Ala His Asn Ile Leu Pro Arg Asn
    290                 295                 300

Val Leu Asn Leu Pro Arg Tyr Asp Tyr Ser Gly Asn Asp Leu Gly Asn
305                 310                 315                 320

Val Tyr Ser Lys Asp Ala Thr Ser Phe Arg Val Trp Ala Pro Thr Ala
                325                 330                 335

Ser Asn Val Gln Leu Leu Tyr Asn Ser Glu Lys Gly Ser Ile Thr
            340                 345                 350

Lys Gln Leu Glu Met Gln Lys Ser Asp Asn Gly Thr Trp Lys Leu Gln
        355                 360                 365

Val Ser Gly Asn Leu Glu Asn Trp Tyr Tyr Leu Tyr Gln Val Thr Val
```

```
            370                 375                 380
Asn Gly Thr Thr Gln Thr Ala Val Asp Pro Tyr Ala Arg Ala Ile Ser
385                 390                 395                 400

Val Asn Ala Thr Arg Gly Met Ile Val Asp Leu Lys Ala Thr Asp Pro
                405                 410                 415

Ala Gly Trp Gln Gly Asp His Glu Gln Thr Pro Ala Asn Pro Val Asp
            420                 425                 430

Glu Val Ile Tyr Glu Ala His Val Arg Asp Phe Ser Ile Asp Ala Asn
                435                 440                 445

Ser Gly Met Lys Asn Lys Gly Lys Tyr Leu Ala Phe Thr Glu His Gly
            450                 455                 460

Thr Lys Gly Pro Asp His Val Lys Thr Gly Ile Asp Ser Leu Lys Glu
465                 470                 475                 480

Leu Gly Ile Thr Thr Val Gln Leu Gln Pro Val Glu Glu Phe Asn Ser
                485                 490                 495

Ile Asp Glu Thr Gln Pro Asp Thr Tyr Asn Trp Gly Tyr Asp Pro Arg
            500                 505                 510

Asn Tyr Asn Val Pro Glu Gly Ala Tyr Ala Thr Thr Pro Glu Gly Thr
            515                 520                 525

Ala Arg Ile Thr Glu Leu Lys Gln Leu Ile Gln Ser Leu His Gln Gln
            530                 535                 540

Arg Ile Cys Val Thr Met Asp Val Val Tyr Asn His Thr Phe Asp Val
545                 550                 555                 560

Met Val Ser Asp Phe Asp Lys Ile Val Pro Gln Tyr Tyr Arg Thr
                565                 570                 575

Asp Ser Asn Gly Asn Tyr Thr Asn Gly Ser Gly Cys Gly Asn Glu Phe
            580                 585                 590

Ala Thr Glu His Pro Met Ala Gln Lys Phe Val Leu Asp Ser Val Asn
                595                 600                 605

Tyr Trp Val Asn Glu Tyr His Val Asp Gly Phe Arg Phe Asp Phe Met
            610                 615                 620

Ala Leu Leu Gly Lys Asp Thr Met Ala Lys Ile Ser Asn Glu Leu His
625                 630                 635                 640

Ala Ile Asn Pro Gly Ile Val Leu Tyr Gly Glu Pro Trp Thr Gly Gly
                645                 650                 655

Thr Ser Gly Leu Ser Ser Asp Gln Leu Val Thr Lys Gly Gln Gln Lys
            660                 665                 670

Gly Leu Gly Ile Gly Val Phe Asn Asp Asn Ile Arg Asn Gly Leu Asp
            675                 680                 685

Gly Asn Val Phe Asp Lys Thr Ala Gln Gly Phe Ala Thr Gly Asp Pro
690                 695                 700

Asn Gln Val Asp Val Ile Lys Asn Gly Val Ile Gly Ser Ile Gln Asp
705                 710                 715                 720

Phe Thr Ser Ala Pro Ser Glu Thr Ile Asn Tyr Val Thr Ser His Asp
                725                 730                 735

Asn Met Thr Leu Trp Asp Lys Ile Leu Ala Ser Asn Pro Ser Asp Thr
                740                 745                 750

Glu Ala Asp Arg Ile Lys Met Asp Glu Leu Ala His Ala Val Val Phe
            755                 760                 765

Thr Ser Gln Gly Val Pro Phe Met Gln Gly Gly Glu Glu Met Leu Arg
            770                 775                 780

Thr Lys Gly Gly Asn Asp Asn Ser Tyr Asn Ala Gly Asp Ser Val Asn
785                 790                 795                 800
```

```
Gln Phe Asp Trp Ser Arg Lys Ala Gln Phe Lys Asp Val Phe Asp Tyr
            805                 810                 815

Phe Ser Ser Met Ile His Leu Arg Asn Gln His Pro Ala Phe Arg Met
        820                 825                 830

Thr Thr Ala Asp Gln Ile Lys Gln Asn Leu Thr Phe Leu Glu Ser Pro
    835                 840                 845

Thr Asn Thr Val Ala Phe Glu Leu Lys Asn Tyr Ala Asn His Asp Thr
850                 855                 860

Trp Lys Asn Ile Ile Val Met Tyr Asn Pro Asn Lys Thr Ser Gln Thr
865                 870                 875                 880

Leu Asn Leu Pro Ser Gly Asp Trp Thr Ile Val Gly Leu Gly Asp Gln
                885                 890                 895

Ile Gly Glu Lys Ser Leu Gly His Val Met Gly Asn Val Gln Val Pro
            900                 905                 910

Ala Ile Ser Thr Leu Ile Leu Lys Gln
            915                 920

<210> SEQ ID NO 5
<211> LENGTH: 44
<212> TYPE: DNA
<213> ORGANISM: Artificial Sequence
<220> FEATURE:
<223> OTHER INFORMATION: synthetic

<400> SEQUENCE: 5
taagaaggag ataccatg gacagcacca gtaccaaggt catc                    44

<210> SEQ ID NO 6
<211> LENGTH: 47
<212> TYPE: DNA
<213> ORGANISM: Artificial Sequence
<220> FEATURE:
<223> OTHER INFORMATION: synthetic

<400> SEQUENCE: 6
gtggtggtgg tggtgctcga gttactgctt aaggatcaaa gtggaga              47

<210> SEQ ID NO 7
<211> LENGTH: 31
<212> TYPE: DNA
<213> ORGANISM: Artificial Sequence
<220> FEATURE:
<223> OTHER INFORMATION: synthetic

<400> SEQUENCE: 7
ggaattcgac agcaccagta ccaaggtcat c                                31

<210> SEQ ID NO 8
<211> LENGTH: 34
<212> TYPE: DNA
<213> ORGANISM: Artificial Sequence
<220> FEATURE:
<223> OTHER INFORMATION: synthetic

<400> SEQUENCE: 8
gctctagatt actgcttaag gatcaaagtg gaga                             34
```

PULLULANASE AND USE THEREOF

REFERENCE TO AN ELECTRONIC SEQUENCE LISTING

The contents of the electronic sequence listing (16029647sequenceListing20180930.txt; Size: 24,000 bytes; and Date of Creation: Sep. 30, 2018) is herein incorporated by reference in its entirety.

CROSS-REFERENCE TO RELATED APPLICATION

This application claims the priority of Chinese Patent No. 201810527491.3 filed on May 29, 2018 and entitled "Pullulanase and Use Thereof".

TECHNICAL FIELD

The present disclosure relates to the enzyme engineering technical field, especially relates to a pullulanase as well as preparation and use thereof.

BACKGROUND

A pullulanase is a starch debranching enzyme, which can hydrolyze alpha-1,6 glucosidic bond of polysaccharides so that the amylose can be converted into amylopectin to the maximum extent. The pullulanase has very important application in the starch processing industry, and it can improve on a large scale the utilization rate and the production efficiency of the starch, and is relatively well applied to production of glucose syrup, maltose syrup and beer.

In the production of glucose, pullulanase and glucoamylase are used together for a saccharification process, and the yield of glucose is increased by reducing the content of the oligosaccharide by using the pullulanase, and the dosage of the glucoamylase can be reduced.

The pullulanase can also be used in the beer industry, it can be added in the saccharification or fermentation process to improve the fermentation capability of beer wort.

In 1961, *Aerobacter aerogenes* which can produce pullulanase was first found by people, and good enzymatic properties of the pullulanase were reported. Since then, a variety of microorganisms capable of producing pullulanase were found by researchers in various countries through extensive research, such as *Bacillus Cereus* var. *Mycoides, Bacillus Acidopullulyticus, Bacillus Subtilis*, and *Clostridum Themosulfurogenes*. But most of the strains for producing pullulanase at present have no industrial value. The present disclosure will provide a high-activity pullulanase by means of genetic engineering.

SUMMARY OF THE INVENTION

In order to achieve the aim, the present disclosure provides a pullulanase mutant and a gene thereof. According to the method disclosed by the invention, an Error-prone PCR (polymerase chain reaction) technology is used, so that the pullulanase coding gene pul from *Bacillus Acidopullulyticus* is subjected to random mutation to obtain a pullulanase mutant gene pulm. The specific enzyme activity of the mutant is increased by 57.03% compared with that of the original gene, and a high-activity pullulanase was obtained by expressing in *Pichia Pastoris*.

DETAILED DESCRIPTION

In the present disclosure, the following definitions are adopted:

1. The amino acid and DNA nucleic acid sequence naming method:

The amino acid residues are named by the three-letter code form specified by the IUPAC nomenclature. The DNA nucleic acid sequence adopts a universally accepted IUPAC nomenclature.

2. Identification of pullulanase mutant

The form of "original amino acid position substituted amino acid" was adopted to express the mutated amino acid in pullulanase mutant, such as Gly547Cys, represents that the amino acid which position number is 547 is Gly in the original pullulanase but is replaced to Cys in the pullulanase mutant, the number of the positions corresponds to the amino acid sequence number of the wild type pullulanase in SEQ ID NO: 2.

In the present disclosure, the original pullulanase is represented by PUL, the amino acids sequence is shown in SEQ ID NO: 2. The mutated pullulanase is represented by PULM, the amino acids sequence is shown in SEQ ID NO:4. The gene encoding PUL is represented by pul, shown in SEQ ID NO: 1, the gene encoding PULM is represented by pulm, shown in SEQ ID NO: 3.

| Pullulanase | Nucleotide | | | Amino acids | | |
|---|---|---|---|---|---|---|
| | No. 1639 | No. 1646 | No. 1867 | No. 547 | No. 549 | No. 623 |
| PUL | G | A | C | Gly | Asn | Leu |
| PULM | T | C | T | Cys | Thr | Phe |

The host cell used for expressing the pullulanase mutant is *Pichia Pastoris* SMD 1168, the expression vector is pGAPZαC.

Beneficial Effects:

1. According to the method disclosed by the invention, the wild type pullulanase gene is randomly mutated by using Error-prone PCR technology, the pullulanase mutant PLUM is obtained, and the specific enzyme activity of the pullulanase mutant PLUM is improved by 57.03% compared with that of the wild-type pullulanase.

2. The mutant site of the pullulanase mutant mentioned in the invention provides a new direction and revelation for research of pullulanase in future.

Figure 2:
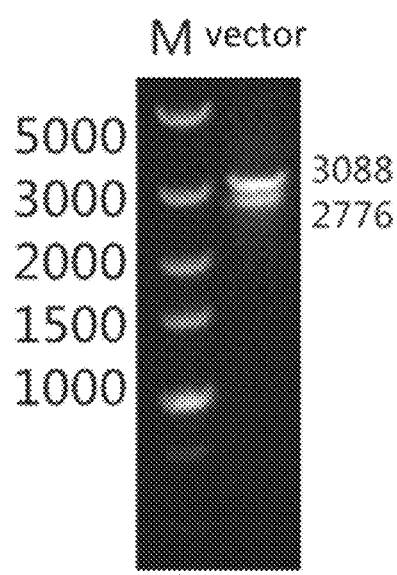

wherein, M is marker; plum is the product of Error-prone PCR;

FIG. 2 is a double-enzyme digestion verification graph of pGAPZαC-pulm;

wherein, M is marker; Vector is the product of double-enzyme digestion.

EXAMPLES

In order to enable the purpose, the technical scheme and the advantages of the invention to be clearer, the present invention is further described in detail with reference to specific examples. It should be understood that the specific examples described herein are only used to explain the present invention and are not intended to limit the present invention.

Example 1 Obtaining of the Genome DNA of *Bacillus Acidopullulyticus*

The wild type pullulanase mature peptide gene pul was from *Bacillus Acidopullulyticus* stored in the applicant's laboratory. The genome DNA was extracted by the method comprising the following steps:

(1) an inoculating loop of *Bacillus Acidopullulyticus* was picked from a flat plate and inoculated into a medium, then cultured at 30° C., 200 rpm for one night;

(2) the culture solution was centrifuged at 12000 r/min for 10 minutes, and then the thallus was harvested in the centrifuge tube;

(3) 1 mL solution I (50 mmol/L Glucose; 25 mmol/L Tris-HCl, pH8.0; 10 mmol/L EDTA, pH8.0), 150 μL lysozyme solution were added to the thallus, and digested at 37° C. for 30 minutes;

(4) 300 μL solution II (0.2 mol/L NaOH; 1% SDS) was added thereto, then the centrifuge tube was inverted for 5 minutes;

(5) equal volume of solution III (saturated phenol:chloroform=1:1) was added, mixed uniformly, and then the mixed solution was centrifuged at the room temperature, 12000 r/min for 10 minutes, then the supernatant was transferred to another clean EP tube, and the organic phase and protein precipitate in lower layer were abandoned.

(6) the above supernatant was repeatedly extracted twice, and extracted with equal volume of chloroform for one time, so as to remove the trace amounts of phenol;

(7) a DNA was precipitated by adding 2-fold volume of absolute ethyl alcohol, then centrifuging at 12000 r/min for 10 minutes, removing the resulting supernatant, and washing the resulting precipitate with 70% ethanol (500 μL) for two times;

(8) the EP tube was inverted and aired on a filter paper, then the DNA was dissolved by TE buffer solution, and preserved at −20° C. for later use.

Example 2 Obtaining of the Mutator Gene of Pullulanase

1. Random Mutation

Random mutation was carried out on the basis of the error-prone PCR (polymerase chain reaction) technology, and a high-activity pullulanase gene was obtained (TaKaRa Taq DNA polymerase was used).

Primers were designed as follows:

```
Forward primer P1(SEQ ID No. 5):
5'-TAAGAAGGAGATATACCATGGACAGCACCAGTACCAAGGTCAT
C-3'

Reverse primer P2(SEQ ID No. 6):
5'-GTGGTGGTGGTGGTGCTCGAGTTACTGCTTAAGGATCAAAGTG
GAGA-3'
```

The amplification template was the genome DNA obtained in example 1, the reaction system of the amplification was as follows:

| | |
|---|---|
| 10× Tag PCR buffer | 5 μL |
| dNTPs (2 mmol/L each) | 5 μL |
| Forward primer P1 (10 μmol/L) | 1.5 μL |
| Reverse primer P2 (10 μmol/L) | 1.5 μL |
| 25 mmol/L MgCl$_2$ | 11 μL |
| 5 mmol/L MnCl$_2$ | 5 μL |
| Amplification template (genome DNA) | 20 pmol |
| TagDNA polymerase | 1 μL |
| ddH$_2$O | complement to 50 μL |

The amplification conditions were as follows: the reaction system was pre-denatured at 95° C. for 3 minutes; denatured at 95° C. for 60 seconds; and annealed at 61° C. for 60 seconds, extended at 72° C. for 180 seconds; after 30 cycles, the reaction system was incubated at 72° C. for 10 minutes, and then stored at 4° C.

Figure 1:
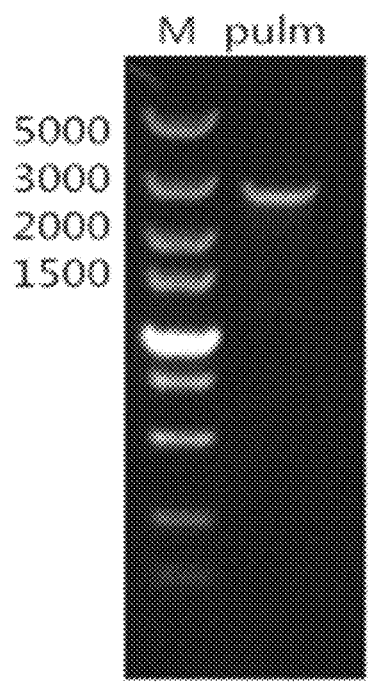
FIG. 1 is a Error-prone PCR product electrophoresis image.

The PCR amplification product was detected by 1.0% agarose gel electrophoresis, a band of about 2800 bp was observed (FIG. 1). The PCR amplification product does not need to be treated, which can be instantly used for the construction of recombinant vector, and also can be stored for a long time at −20° C.

2. Linearization of the Expression Vector

A conventional restriction enzyme of Takara was used to linearize the PET-28 plasmid, the reaction system was as follows:

| | |
|---|---|
| Nco I | 5 μL |
| Xho I | 5 μL |
| 10*K buffer | 10 μL |
| 0.1% BSA | 10 μL |
| pET-28a | 5 μg |
| ddH$_2$O | complement to 100 μL |

The linearization conditions are as follows: the reaction system was incubated at 37° C. for 3 hours; at 65° C. for 20 minutes, and then stored at 4° C. The linearized product can be immediately used for the construction of expression vector and can also be stored for a long time at −20° C.

3. Construction of Expression Vector Library

The pul mutant expression vector library was constructed by using the one-step ligase of ClonExpress II of Vazyme to connect the error-prone PCR product with the linearized PET-28a. In order to ensure sufficient storage capacity, five connecting reactions were carried out at the same time, the connecting system was 100 μL in total.

The connecting system comprised the following components:

| | |
|---|---|
| 5*CE II buffer | 4 μL |
| Error-prone PCR product | 112 ng |
| Linearized PET-28a | 110 ng |
| Exnase II | 2 μL |
| ddH$_2$O | complement to 20 μL |

Note:
the connecting system was prepared in an ice bath.

The reaction conditions were as follows: the connecting system was incubated at 37° C. for 30 minutes; and at 4° C. for 5 minutes.

After the reaction was finished, the product can be stored at 4° C. in a short term or stored at −20° C. in a long term.

4. Construction of Pul Mutant Expression Strain Library

20 μL of the pul mutant expression vector obtained in step 3 was transformed into the expression strain *Escherichia coli* BL21 in the following manner:

The competent cells of *E. coli* BL21 (100 μL for each) were taken out from −80° C., and placed on ice to be dissolved, then immediately 20 μL of the pul mutant expression vector was added thereto in an aseptic environment after dissolving. Then, the system was placed on ice for 30 minutes, and heat shocked by a water bath for 90 s at 42° C., cooled on ice for 1.5 min. Afterwards, 900 μL of LB medium was added thereto, and a pre-cultivation was performed at 37° C., 200 r/min for 30 min, then a centrifugation was carried out for 2 min at the speed of 3000 rpm. The supernate of 600 μL was skimmed, and the residual supernate were uniformly mixed with the resulting thallus sediment through blowing-suction by a pipettor to obtain a concentrated bacterial solution. Further, each 100 μL of the concentrated bacterial solution was spreaded on an LB flat plate with kanamycin resistance, each group was provided with four parallel, and all inverted on the constant-temperature incubator to subject to a cultivation at 37° C. for one night.

Finally, 20 flat plates with recombinant strain were obtained, sealed with sealing film and placed at 4° C. for short-term storing.

5. Screening of the High-activity Pullulanase Gene

At least 2000 positive transformants were selected from the 20 flat plates with recombinant strain of step 4, and each of the positive transformants was divided to two parts, one was inoculated into a new flat plate with kanamycin resistance which used for strain preservation; meanwhile, the other was inoculated in a 96-well plate with 200 μL LB liquid medium for each well (which contains 30 μg/mL of kanamycin).

The flat plate used for strain preservation was cultured overnight at 37° C., and then sealed with a sealing film, stored at 4° C.

The 96-well plates were cultured at 37° C., 200 r/min. When $OD_{600}$ reached 0.6, each of the wells was added with IPTG (final concentration of 1 mmol/L), and then an induction was performed at 16° C. for 16 h followed by a centrifugation at 4° C. 4000 r/min for 15 minutes to obtain the thallus. The obtained thallus was resuspended in 15 mL of pre-cooled PBS buffer solution with pH 7.4, and a cell disruption treatment was performed to crush cells by using a low-temperature ultrahigh-pressure continuous flow cell disruption instrument. After the disruption treatment was completed, a centrifugation was carried out at 4° C., 12000 r/min for 45 minutes to collect the supernate to obtain a crude enzyme solution. Then, an enzyme activity measurement was carried out on the crude enzyme solution. The measurement result showed that the enzyme activity of the mutant pulm is the highest, it was improved by 57.03% compared with that of the wild type pul. The mutant pulm was sent to Beijing Huada Gene Science and Technology Co., Ltd. to finish the gene sequencing by using a universal primer T7/T7 ter, the sequencing result showed that the mutator gene-pulm has a nucleotide sequence as shown in SEQ ID NO. 3 which encoded an amino acid with Gly547Cys, Asn549Thr and Leu623Phe compared with the PUL.

Example 3 Construction of a Recombinant *Pichia Pastoris* Freely Expressing the Pullulanase Mutant The high-activity pullulanase gene (pulm) was linked with a *Pichia Pastoris* secretory expression vector-pGAPZαC to construct the recombinant expression vector pGAPZαC-pulm, and tansformed into the *Pichia Pastoris*.

1. Construction of the Recombinant Expression Vector pGAPZαC-Pulm

The pGAPZαC was a fusion expression vector and provided with an alpha factor secreting signal peptide which can secrete protein out of *Pichia pastoris* cells made the protein convenient to be purified; meanwhile, the Zeocin resistant gene on pGAPZαC was used for preserving and screening of recombinant strains;

The MCS (multiple cloning site) of pGAPZαC include EcoRI, PmlI, XhoI, NotI and XbaI. EcoRI/XbaI were chosen to construct the recombinant expression vector pGAPZαC-pulm. Primers used to amplify pulm and add restriction enzyme cutting site were as follows:

```
Forward primer P5(SEQ ID No. 7):
GGAATTCGACAGCACCAGTACCAAGGTCATC
(Contains the EcoRI site)

Reverse primer P6(SEQ ID No. 8):
GCTCTAGATTACTGCTTAAGGATCAAAGTGGAGA
(Contains the XbaI site)
```

The amplification template was pET28a-pulm, the amplification system was as follows (The Pyrobest DNA Polymerase of Takara was used in this system):

| Amplification template DNA | 500 ng |
|---|---|
| Pyrobest DNA Polymerase (5 U/μL) | 0.25 μL |
| 10× Pyrobest buffer II | 5 μL |
| dNTPs (2.5 mmol/L each) | 4 μL |
| Forward primer P5 (10 μmol/L) | 1.5 μL |
| Reverse primer P6 (10 μmol/L) | 1.5 μL |
| ddH$_2$O | complement to 50 μL |

The amplification conditions were as follows: pre-denaturation at 98° C. for 3 minutes; denaturation at 98° C. for 10 seconds; annealing at 61° C. for 60 seconds, and extension at 7210 for 180 seconds. This process repeats for 30 cycles. Then, incubation was performed at 72° C. for 10 minutes. And the product was stored at 4° C. The PCR amplification product (pulm) was detected by 1.0% agarose gel electrophoresis, a band of about 2800 bp was observed. After being purified by the DNA Purification Kit the PCR amplification product can be immediately used for the construction of the recombinant expression vector, and also can be stored for a long time at −20° C.

The purified pulm and the pGAPZαC were respectively subjected to enzyme digestion by using the EcoRI/XbaI, the enzyme digestion system was as follows:

| EcoR I | 5 μL |
|---|---|
| Xba I | 5 μL |
| 10*M buffer (from TaKaRa) | 10 μL |
| DNA | 5 μg |
| ddH$_2$O | complement to 100 μL |

1.0% agarose gel electrophoresis was used to separate the enzyme digestion product, the pGAPZαC and pulm fragments were recycled by gel extraction and linked by T4 ligase overnight. The connecting system was as follows:

| T4 ligase | 1 μL |
|---|---|
| 10* T4 Buffer | 2.5 μL |

| | |
|---|---|
| pGAPZaC | 0.03 pmol |
| pulm | 0.3 pmol |
| ddH2O | complement to 25 μL |

After the preparation of the connecting system was completed, the system was kept at 16° C. for 16 hours for connecting, and then stored at 4° C. Thus, the recombinant expression vector pGAPZαC-pulm was completed.

The heat shock method was used to transform the pGAPZαC-pulm into *E. coli* DH5α competent cells. And the competent cells were spreaded onto the LB flat plate with Zeocin resistance and then cultured overnight. Then, the positive transformants were selected for plasmids extraction, then the plasmids were verified by enzyme digestion (FIG. 2) and sequencing was done to confirm the right recombinant expression vector pGAPZαC-pulm was obtained.

2. Construction and Screening of Recombinant Strain Expressing High Activity Pullulanase Mutant (1) Preparation of the Linearized Plasmid DNA Before transformed into the *Pichia Pastoris*, the recombinant expression vector pGAPZαC-pulm needed to be linearized, so that the integration efficiency of the plasmid on the *Pichia Pastoris* chromosome will be improved. And the linearization was completed by restriction endonuclease BspHI.

(2) The Transformation of Linearized pGAPZαC-Pulm into *Pichia Pastoris*, Identification of Positive Transformant, and Screening of Pullulanase Strain with High-Productivity ① 80 μL of *Pichia Pastoris* SMD 1168 competent cells and 10 μg of the linearized pGAPZαC-pulm were added to a 1.5 ml pre-cooled centrifuge tube and mixed evenly, then transferred into a pre-cooled conversion cup;

② the conversion cup of step ① was placed in a ice bath for 5 min, and a electroporation was carried out on *Pichia Pastoris* SMD1168 according to the parameters recommended by the electroporation device;

③ after the pulse, 1 ml of pre-cooled 1 mol/L sorbitol solution was added into the conversion cup immediately to obtain a transformation solution, then the transformation solution was transferred into a new 1.5 mL centrifuge tube;

④ after a static culture at 30° C. for 1.5 h, 200 μL of the transformation solution was sucked and spread onto the MD medium;

⑤ a cultivation was carried out at 30° C. until the transformants appeared.

⑥ a single colony of the transformants was selected and dissolved in 10 μL of deionized water to get the bacterial suspension. 2 μL of the bacterial suspension was taken and added with Lyticease to react for 10 min at 30° C. Then, the resulting reaction solution was placed into a refrigerator with the temperature of −80° C. to be frozen for 10 min, so that the cell wall of the yeast was cracked to release the genome. The released genome was used as a template for PCR. The positive transformant was identified by taking *Pichia Pastoris* SMD 1168 with empty pGAPZαC as a control.

⑦ on the basis that the positive transformant has been identified, screening of the high geneticin-resistant transformant was performed by using flat plate containing different concentrations of geneticin, and then the enzyme activity of the pullulanase of the high geneticin-resistant transformant was measured respectively to obtain the high-yield strain SMD 1168/pGAPZαC-pulm of pullulanase.

Example 4 Expression and Preparation of Pullulanase Mutant by SMD 1168/pGAPZαC-Pulm The recombinant bacterium SMD 1168/pGAPZαC-pulm was inoculated to a YPD liquid medium and cultured at 30° C., 250 r/min for 24 h. Then the culture was transferred into a fresh BMGY medium at the inoculation amount of 1%, and cultured at 30° C., 250 r/min for 24 hours, and a centrifugation was carried out for 5 minutes at 6000 r/min to obtain the thallus. Then, the thallus was transferred into a BMMY medium, and cultured at 30° C., 250 r/min for 120 hours to obtain the crude enzyme liquid of the pullulanase. Then a high-activity pullulanase was precipitated by salt fractionation of the crude enzyme liquid, wherein the protein precipitate was collected, dissolved, desalted by dialysis, and treated by an ion exchange chromatography and a gel chromatography, and then the freeze drying, so as that the high-activity pullulanase pure enzyme powder was obtained.

About 183 mg pure enzyme powder of pullulanase was obtained by every liter of culture medium. Example 5 Determination of the pullulanase activity 1. Assay Method DNS method: 50 μL appropriately diluted pullulanase solution was added to 450 μL buffer (the 5% pulullan solution and the buffer solution with pH5.0 were uniformly mixed in a ratio of 1:8), and then sufficient mixing was done to react 30 min at 50° C., and then 500 μL DNS solution was added to terminate the reaction. A water bath was carried out for 10 minutes at 100° C., then $OD_{540}$ values were measured.

2. Result

The specific activity of PUL and PULM were assayed as 370 U/mg and 581 U/mg, it was shown that the specific activity has been improved by 57.03% after the mutation.

Definition of specific enzyme activity: under determination conditions, the enzyme required by generating 1 μmol of reducing sugar (Glucose) per minute from the hydrolyzation of pulullan is defined as an enzyme activity unit (U), the specific enzyme activity means the number of enzyme activity unit in per unit weight of protein, which was generally represented by U/mg protein.

The SMD 1168/pGAPZαC-pulm and *Bacillus Acidopullulyticus* were fermented as the method described in example 4, and then the pullulanase activity of the fermentation broth thereof was measured. It was shown that SMD 1168/pGAPZαC-pulm was 106.4 U/ml and *Bacillus Acidopullulyticus* was 7.4 U/mL.

The above embodiments only express several embodiments of the present invention, the description is specific and detailed, but is not to be construed as limiting the scope of the patent. It should be noted that for one of ordinary skill in the art, the above embodiments can also make a plurality of deformation, combinations and improvements without departing from the concept of the present invention, thereof, all of which belong to the scope of protection of this patent. Therefore, the protection scope of the invention should be determined by the appended claims.

We claim:
1. A pullulanase mutant having pullulanase activity, wherein, the said pullulanase mutant comprises the amino acid sequence of SEQ ID NO.4.

* * * * *